United States Patent [19]

Baker et al.

[11] E Patent Number: Re. 33,300

[45] Reissued Date of Patent: Aug. 14, 1990

[54] OXIRANES

[75] Inventors: Stephen R. Baker, Eversley; William B. Jamieson, Horsell; Alec Todd, Wokingham, all of England

[73] Assignee: Eli Lilly and Company, Indianapolis, Ind.

[21] Appl. No.: 430,697

[22] Filed: Nov. 1, 1989

Related U.S. Patent Documents

Reissue of:

[64] Patent No.: 4,665,189
Issued: May 12, 1987
Appl. No.: 635,863
Filed: Jul. 30, 1984

[30] Foreign Application Priority Data

Aug. 3, 1983 [GB] United Kingdom ..... 8320943

[51] Int. Cl.[5] ..... C07D 405/10; C07D 303/8; C07D 303/12

[52] U.S. Cl. ..... 548/252; 549/551; 549/554; 549/556

[58] Field of Search ..... 548/252; 549/551, 554, 549/556

[56] References Cited

FOREIGN PATENT DOCUMENTS 68739 1/1983 European Pat. Off. .

OTHER PUBLICATIONS

Prelog, V. et al, Helv. Chem. Acta, 27, 1209 (1944)
Chem. Abstracts 40:848(8).
Russell, G. A. et al., J. Org. Chem. 31(9) 2854 (1966).
Kano, S. et al, J.C.S. Chem Comm 785 (1978).
Eberbach et al., *Chem. Ber.*, 114, 2979 (1981).
Eberbach et al., *Tetrahedron Letters*, (48) 4649 (1979).
Tamura et al., *Synthesis*, (10), 693 (1977).
Braun et al., *Tetrahedron Letters*, 41, 4033 (1973), p. 4035.

*Primary Examiner*—David B. Springer
*Attorney, Agent, or Firm*—Robert A. Conrad; Leroy Whitaker

[57] ABSTRACT

There are described compounds of formula

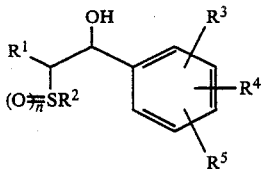

(I)

in which n is 0, 1 or 2, $R^1$ is a hydrocarbyl group optionally substituted with an optionally substituted phenyl group and containing from 5 to 30 carbon atoms, $R^2$ is optionally substituted phenyl or $C_{1-10}$alkyl optionally substituted by one or more substituents selected from optionally protected hydroxyl, optionally protected carboxyl, nitrile, optionally protected tetrazolyl, —$COR^6$ where $R^6$ is $C_{1-4}$alkyl, $C_{1-4}$alkoxy, an optionally protected amino acid residue or —$NR_2^7$ where each $R^7$ is hydrogen or $C_{1-4}$alkyl, and —$NHR^8$ where $R^8$ is hydrogen, a protecting group, an optionally protected amino acid residue, $C_{1-4}$alkyl or —$COR^9$ where $R^9$ is $C_{1-4}$alkyl or $C_{1-4}$alkoxy, and $R^3$, $R^4$ and $R^5$ are each selected from hydrogen, carboxyl, $C_{2-5}$alkoxycarbonyl, $C_{1-4}$alkyl, $C_{1-4}$alkoxy, hydroxyl, optionally protected tetrazolyl, halo, trifluoromethyl, nitrile, nitro and —$CONR_2^{10}$ where each $R^{10}$ is hydrogen or $C_{1-4}$alkyl; and salts thereof. The compounds are leukotriene antagonists.

2 Claims, No Drawings

OXIRANES

Matter enclosed in heavy brackets [ ] appears in the original patent but forms no part of this reissue specification; matter printed in italics indicates the additions made by reissue.

This invention relates to novel compounds and their use as pharmaceuticals.

The compounds of the invention are of the formula

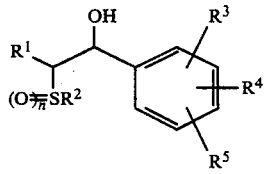

(I)

in which n is 0, 1 or 2, $R^1$ is a hydrocarbyl group optionally substituted with an optionally substituted phenyl group and containing from 5 to 30 carbon atoms, $R^2$ is optionally substituted phenyl or $C_{1-10}$ alkyl optionally substituted by one or more substituents selected from optionally protected hydroxyl, optionally protected carboxyl, nitrile, optionally protected tetrazolyl, —$COR^6$ where $R^6$ is $C_{1-4}$alkyl, $C_{1-4}$alkoxy, an optionally protected amino acid residue or —$NR_2^7$ where each $R^7$ is hydrogen or $C_{1-4}$alkyl, and —$NHR^8$ where $R^8$ is hydrogen, a protecting group, an optionally protected amino acid residue, $C_{1-4}$alkyl or —$COR^9$ where $R^9$ is $C_{1-4}$alkyl or $C_{1-4}$alkoxy, and $R^3$, $R^4$ and $R^5$ are ech selected from hydrogen, carboxyl, $C_{2-5}$akoxycarbonyl, $C_{1-4}$alkyl, $C_{1-4}$alkoxy, hydroxyl, optionally protected tetrazolyl, halo, trifluoromethyl, nitrile, nitro and —$CONR_2^{10}$ where each $R^{10}$ is hydrogen or $C_{1-4}$alkyl; and salts thereof.

The compounds of the invention, in unprotected form, have been shown to be pharmacologically active in tests which demonstrate their antagonist effect on leukotriene receptors and indicate their use in the treatment of allergic disorders.

In the above general formula, the optionally substituted hydrocarbyl group includes an optionally substituted alkyl group or optionally substituted alkenyl and alkynyl groups, the substituents on such groups being phenyl and substituted phenyl. The hydrocarbyl group preferably contains from 5 to 20 carbon atoms, for example from 10 to 20 carbon atoms and especially from 10 to 15 carbon atoms. When $R^1$ is alkyl it can be branched or unbranched and is preferably one containing 10 to 15 carbon atoms. When $R^1$ is alkenyl it can be branched or unbranched preferably containing 10 to 15 carbon atoms, such as for example 12 to 15. The alkenyl group preferably contains 1 to 4 double bonds and can be, for example, of the general formula $$R^{11}CH{=}CHCH{=}CH-$$

where $R^{11}$ is $C_{7-11}$alkyl or $CH_3(CH_2)_nCH{=}CH{-}CH_2{-}CH{=}CH-$ where n is 0 to 4. It will be appreciated that such double bonds provide opportunities for cis-trans isomeric forms. Two especially preferred examples of alkenyl groups are:

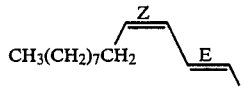

and

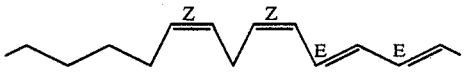

Where $R^1$ is alkynyl it can be branched or unbranched, and preferably contains from 10 to 15 carbon atoms having 1 to 4 triple bonds. It is to be understood that such alkynyl groups can also contain one or more, for example, 1 to 3 double bonds in addition to its triple bond or bonds.

When $R^1$ is substituted hydrocarbyl it is substituted by an optionally substituted phenyl ring, preferably phenyl itself, or a phenyl group substituted with one or more, preferably 1 to 3, substituents selected from $C_{1-4}$alkyl, especially methyl, $C_{1-4}$alkoxy, especially methoxy and ethoxy, hydroxy, nitro, cyano, halo, especially chloro, trifluoromethyl, carboxyl, tetrazolyl and —$CONH_2$. When $R^1$ is substituted with an optionally substituted phenyl group it is preferably an alkenyl group.

It is preferred that $R^1$ is one of the above defined alkenyl groups.

With regard to $R^2$, this can be a $C_{1-10}$alkyl group, preferably $C_{1-6}$alkyl, and optionally substituted by one or more, preferably 1 to 3, substituents as defined above. The substituent can be, —$COR^6$ or —$NHR^8$ where $R^6$ and $R^8$ are amino acid residue. Such amino acid residues can be optionally protected by a conventional protecting group and can be derived from any of the commonly occurring amino acids. In the case of $R^6$ the residue is preferably derived from glycine having the value —$NHCH_2COOH$ and in the case of $R^8$ it is preferably derived from aspartic acid or glutamic acid, having the values —$COCH_2CH(NH_2)COOH$ and —$COCH_2CH_2CH(NH_2)COOH$, respectively. Examples of the $SR^2$ group include cysteinyl, cysteinylglycinyl and glutathionyl of formulae —$SCH_2CH(NH_2)COOH$, —$SCH_2CH(NH_2)CONHCH_2COOH$ and $$-SCH_2\underset{\underset{NHCOCH_2CH_2CH(NH_2)COOH,}{|}}{CH}CONHCH_2COOH$$

respectively.

Preferably $R^2$ is an alkyl group substituted with 1 to 3 substituents selected from carboxyl, nitrile, tetrazolyl, and —$COR^6$ where $R^6$ is —$NR_2^7$ or $C_{1-4}$alkoxy.

A particularly preferred value of $R^2$ is of the following formula:

$$-(CH_2)_xR^{12}$$

where x is 1 to 5 and $R^{12}$ is carboxyl, nitrile, —$CONH_2$ or tetrazolyl. Most preferred are groups in which x is 2 and/or $R^{12}$ is carboxyl or tetrazolyl.

As mentioned above, $R^2$ can be optionally substituted phenyl and it can be any of the values defined above when $R^1$ bears an optionally substituted phenyl group. Preferably the phenyl ring is substituted with 1 to 3 substituents selected from carboxyl, tetrazolyl and $CONH_2$, and especially a single carboxyl substituent.

As defined above, the groups $R^3$, $R^4$ and $R^5$ can be hydrogen, carboxyl, $C_{2-5}$alkoxycarbonyl, $C_{1-4}$alkyl, $C_{1-4}$alkoxy, hydroxyl, optionally protected tetrazolyl, halo, trifluoromethyl, nitrile, nitro and —$CONHR_2^{10}$ where each $R^{10}$ is hydrogen or $C_{1-4}$alkyl. The tetrazolyl group is preferably 1H-tetrazol-5-yl. Preferably there is a single substituent on the phenyl ring and it is preferred that the substituent be nitrile, —$CONH_2$, tetrazolyl or carboxyl, acid substituents such as tetrazolyl and carboxyl being best of all. Maximum biological activity is given by the compounds in which the tetrazolyl or carboxyl group is attached at the ortho or meta positions, and the most preferred groups are of the formula

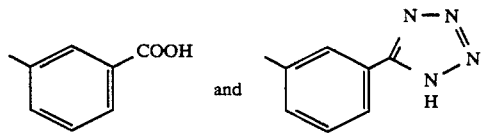

Preferred compounds of formula (I) above are those in which n is 0.

In the above general formulae $C_{1-4}$alkyl means a straight or branched chain alkyl group, for example, methyl, ethyl, propyl, isopropyl, butyl, isobutyl and tertiary butyl, and is preferably methyl or ethyl. Similarly a $C_{1-4}$alkoxy group is any such alkyl group attached through oxygen to the appropriate moiety, and alkoxycarbonyl is a group of the form ROCO— where R is a $C_{1-4}$alkyl group as described above.

When substituents on the compound of formula (I) require protection during preparation they may be protected by conventional protecting groups. Compounds with such protected carboxyl, amino acid residues, amino, hydroxyl and tetrazolyl groups are included in the scope of the invention, through the preferred compounds with optimum biological properties are the unprotected compounds derived from them. Carboxy-protecting groups are the well known ester forming groups used for the temporary protection of acidic carboxylic acid groups. Examples of such groups which have general use are readily hydrolysable groups such as arylmethyl groups, haloalkyl groups, trialkylsilyl groups, alkyl groups, and alkenyl groups. Other carboxy protecting groups are those described by E. Haslam in Protective Groups in Organic Chemistry, Chapter 5. The amino-protecting groups that can be employed in the preparation of the compounds of the invention are also conventional protecting groups. Illustrative of such groups are trihaloacetyl groups especially trifluoroacetyl. Such groups are well known in the art and are discussed, for example, in Peptide Synthesis by M. Bodansky, Y. S. Klausner and M. A. Ondetti, Second Edition (1976) John Wiley & Sons. Any free hydroxy groups present in the compound of the invention may likewise be protected if needed. For example, a hydroxy group on the $R^2$ group of a compound of the formula I, can be protected with a conventional labile ether forming protecting group such as an ether formed with dihydropyran or methylvinyl ether, or by esters formed with the lower alkyl carboxylic acids such as formic, acetic or propionic, or such halogenated acids, for example, chloroacetic acid, dichloroacetic acid or $\beta,\beta$-dichloropropionic acid. Furthermore, it is usually necessary to protect any tetrazolyl group during the process of preparation, and suitable and well known protecting groups for this purpose include the trityl and benzhydryl groups formed by reaction with the appropriate halide in the presence of base for example by reacting the tetrazolyl reactant with trityl chloride and triethylamine.

When the compound of formula (I) bears an acidic function, base addition salts can be prepared and these are to regarded as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms together with other pharmaceutically acceptable salts are particularly preferred, but it is to be understood that other non-pharmaceutical salts are involved in the invention since they may be useful for identification, characterization or purification of the free compound.

When the compound of formula (I) has a basic function acid addition salts can be prepared and these are included in the present invention. Example of such salts are those derived from, preferably non-toxic, inorganic acids such as for example hydrochloric acid, nitric acid, phosphoric acid, sulphuric acid and nitric acid, as well as salts derived from, preferably non-toxic, organic acids such as aliphatic mono- and di-carboxylic acids, phenyl-substituted alkanoic acids, hydroxyalkanoic acids, aromatic acids, and aliphatic and aromatic sulphonic acids.

It will be appreciated that the compounds of formula (I) possess chiral centres at the carbon atoms bearing the hydroxyl and $SR^2$ groups and, accordingly, stereoisomeric forms exist R,R; S,S; R,S; and S,R. Other chiral centres are also possible, depending on the nature of the various substituents, which may lead to further steri-oisomeric forms. Furthermore, as mentioned above, compounds containing $R^1$ alkenyl substituents exhibit cis-trans isomeric forms. All such stereoisomers, and racemic mixtures thereof, are included within the scope of the invention. Isomers can be isolated from racemic mixtures by conventional methods such as by the preparation of diastereoisomers with subsequent liberation of the enantiomers or, alternatively, can be prepared by methods devised to give the pure isomer.

A particular group of compounds according to formula (I) above are those of the following formula

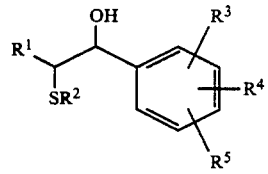

in which $R^1$ is an optionally unsaturated hydrocarbyl group containing from 5 to 30 carbon atoms, $R^2$ is $C_{1-10}$alkyl optionally substituted by one or more substituents selected from optionally protected hyroxyl, optionally protected carboxyl, —$COR^6$ where $R^6$ is $C_{1-4}$alkoxy or an optionally protected amino acid residue, and —$NHR^8$ where $R^8$ is hydrogen, a protecting group, a optionally protected amino acid residue, $C_{1-4}$alkyl or —$COR^9$ where $R^9$ is $C_{1-4}$alkyl or $C_{1-4}$alkoxy, and $R^3$, $R^4$ and $R^5$ are each selected from hydrogen, carboxyl, $C_{2-5}$alkoxycarbonyl, $C_{1-4}$alkyl, hydroxyl, tetrazolyl, halo, trifluoromethyl, nitrile and nitro; and salts thereof.

An especially preferred group of compounds of formula (I) above is of the formula

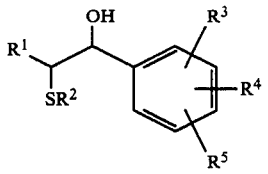

in which $R^1$ is an alkenyl group containing 10 to 20 carbon atoms, $R^2$ is of the formula —$(CH_2)_xR^{12}$ where x is 1 to 5 and $R^{12}$ is carboxyl, nitrile, —$CONH_2$ or tetrazolyl, and $R^3$, $R^4$ and $R^5$ are selected from hydrogen, carboxyl, nitrile, —$CONH_2$ and tetrazolyl; and salts thereof.

Of these compounds the most preferred are those in which $R^1$ is of the formula $R^{11}CH{=}CHCH{=}CH$— where $R^{11}$ is $C_{7-11}$alkyl or $CH_3(CH_2)_nCH{=}CH{-}CH_2{-}CH{=}CH$— and n is 0 to 4, $R^2$ is —$(CH_2)_xR^{12}$ where x is 1 to 5 and $R^{12}$ is carboxyl, nitrile, —$CONH_2$ or tetrazolyl, $R^3$ is nitrile, —$CONH_2$, tetrazolyl or carboxyl, the substituent preferably being at the ortho or meta positions, and $R^4$ and $R^5$ are both hydrogen; salts thereof.

The invention also includes a process for producing a compound of the formula

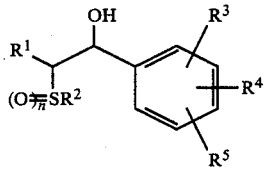

(I)

in which n is 0, 1 or 2, $R^1$ is a hydrocarbyl group optionally substituted with an optionally substituted phenyl group and containing from 5 to 30 carbon atoms, $R^2$ is optionally substituted phenyl or $C_{1-10}$alkyl optionally substituted by one or more substituents selected from optionally protected hydroxyl, optionally protected carboxyl, nitrile, optionally protected tetrazolyl, —$COR^6$ where $R^6$ is $C_{1-4}$alkyl, $C_{1-4}$alkoxy, an optionally protected amino acid residue or —$NR_2^7$ where each $R^7$ is hydrogen or $C_{1-4}$alkyl, and —$NHR^8$ where $R^8$ is hydrogen, a protecting group, an optionally protected amino acid residue, $C_{1-4}$alkyl or —$COR^9$ where $R^9$ is $C_{1-4}$alkyl or $C_{1-4}$-alkoxy, and $R^3$, $R^4$ and $R^5$ are each selected from hydrogen, carboxyl, $C_{2-5}$alkoxycarbonyl, $C_{1-4}$alkyl, $C_{1-4}$alkoxy, hydroxyl, optionally protected tetrazolyl, halo, trifluoromethyl, nitrile, nitro and —$CONR_2^{10}$ where each $R^{10}$ is hydrogen or $C_{1-4}$alkyl; and salts thereof; which comprises reacting a compound of formula

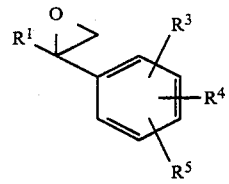

(II)

in which $R^1$ is an optionally substituted alkenyl or alkynyl group, with a thiol of formula $R^2SH$, optionally followed when it is desired to prepare a compound in which n is 1 or 2, by oxidation, or when it is desired to prepare a compound in which $R^1$ is optionally substituted alkyl, by reduction, or by removal of any protecting groups, or by interconversion of an $R^2$, $R^3$, $R^4$ or $R^5$ group.

The reaction of compound of formula (II) with thiol is preferably carried out in an inert organic solvent such as an alcohol, for example methanol, in the presence of a base such as a triethylamine and at a temperature of from 0° C. to 50° C. Thiol reactants containing potential anion especially if it is sterically close to the thiol group are, desirably, protected before reaction.

When it is desired to prepare the sulphoxide compounds in which n is 1 in formula (I) above, the corresponding sulphide in which n is 0 is reacted in substantially equivalent proportions with a suitable oxidising agent such as for example sodium periodate in an aqueus medium such as aqueous methanol at a temperature of, for example, from 0° C. to 50° C. The sulphone compounds in which n is 2 in formula (I) can be prepared by reacting the sulphide with an excess of oxidising agent such as for example potassium persulphate, or by reacting the appropriate sulphoxide with an excess of oxidising agent, both reactions being carried out under similar conditions to those employed in the preparation of the sulphoxide and preferably at a temperature of from 0° C. to 100° C.

It will be appreciated that it may be desired to remove any protecting groups attached to the product of the reacton. Such reactions can readily be carried out by use of a base in an inert organic solvent, such as for example, lithium hydroxide in tetrahydrofuran, or potassium carbonate in methanol, at a temperature of from 0° C. to 80° C., or by use of acid such as hydrochloric acid for removal of protecting groups from tetrazolyl, or by reducton in the case of protected amino groups, by well known procedures described for example in the authorities referred to above.

Also it will be appreciated that one or more of the substituents on the $R^2$ group or $R^3$, $R^4$ and $R^5$ groups can be interconverted. It is often preferred, depending on the nature of the group, that such interconversions are carried out after reaction of compound of formula (II) with thiol.

For example, compounds in which $R^3$, $R^4$ or $R^5$ is $C_{2-5}$alkoxycarbonyl or in which $R^2$ bears such a group can be converted to the corresponding free carboxyl by hydrolysis by means of base in an inert organic solvent, such as for example, lithium hydroxide in tetrahydrofuran. Such methods are well known in the art. Conversely, compounds in which $R^3$, $R^4$ or $R^5$ is $C_{2-5}$alkoxycarbonyl or $R^2$ has such a group can be prepared from the free acid by esterification of the free carboxyl group with the appropriate alcohol or by treatment with alkyl halide in the presence of base. Salts of the free acid can, of course, be prepared simply by reaction with alkali.

Compounds in which $R^3$, $R^4$ or $R^5$ is —$CONHR_2^{10}$ or $R^2$ bears a —$CONR_2^7$ group can be prepared by reacting a compound with an appropriate alkoxycarbonyl substituent with ammonia or the appropriate amine of formula $R_2^{10}NH$ or $R_2^7NH$, respectively, or they can be prepared by the reaction of an amine of formula $R_2^{10}$ NH or $R_2^7NH$ with the appropriate acyl chloride, which can in its turn be derived from the free carboxyl derivative by the reaction of thionyl chloride. Such reactions are well known in the art.

Compounds in which $R^3$, $R^4$ or $R^5$ is a nitrile group or $R^2$ has such a group can be prepared by dehydration of the appropriate amide (—$CONH_2$), a convenient dehydrating agent being, for example, a mixture of triphenylphosphite and carbon tetrachloride.

Compounds in which $R^3$, $R^4$ or $R^5$ is tetrazolyl or $R^2$ has such a group can be prepared by reaction of the cyano derivative prepared as above with, for example sodium azide and ammonium chloride in dimethylformamide. Salts can be prepared from the tetrazolyl derivatives by the addition of base according to standard techniques.

It will be appreciated that the steps of reduction to provide the saturated $R^1$ substituents, oxidation to provide sulphones and sulphoxides, removal of protecting group or interconversion of groups, can be carried out in whatever sequence best suits convenience and the aim of maximising yield.

The reactants of formula $R^2SH$ are known compounds or can be prepared by methods of a type well known in the art. When they bear amino, carboxyl or hydroxyl groups the reaction may benefit in yield if these groups are first protected, but such initial protection is by no means necessary in all cases.

Compounds of formula (II) in which $R^1$ is optionally substituted alkenyl or alkynyl are novel and are included as part of the present invention. They may be prepared by the Wittig reaction of a phosphonium salt of formula $R^{13}CH_2P^+Ph_3Br^-$, $R^{13}$ being an appropriate optionally substituted alkyl, alkenyl or alkynyl group, in the presence of a base such as butyl lithium, with an aldehyde of formula (III) or (IV)

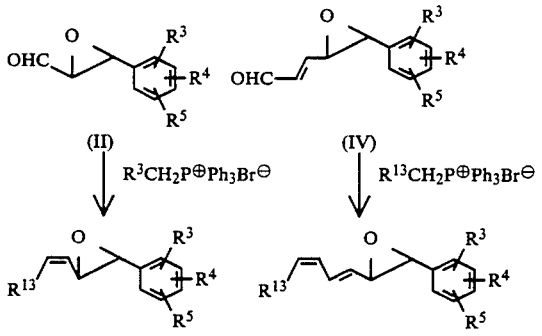

The reaction is generally carried out in a inert organic solvent such as for example, tetrahydrofuran, at a temperature of from −80° C. to 0° C.

Compounds of formula (III) may be prepared from known intermediates by, for example, two principal routes. Firstly, they may be prepared, as racemic mixtures, by oxidation with, for example, hydrogen peroxide and sodium hydrogen carbonate in methanolic solution, of an aldehyde of the formula

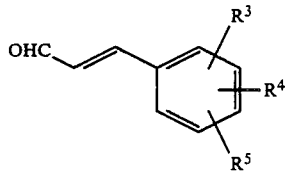

and, in its turn, aldehyde of formula (III) may be converted to one of formula (IV) by reaction with formylmethylenetriphenylphosphorane.

Alternatively, the compounds of formula (III) may be prepared by oxidation of an epoxy alcohol of the formula

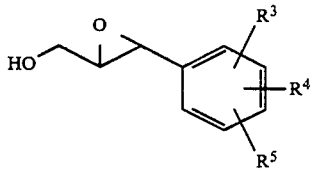

(V)

with an oxidising agent such as, for example, chromium trioxide in pyridine. Compounds of formula (V) can be prepared in stereospecific form and since the steric configuration is retained on oxidation to provide the aldehyde of formulae (III) and, ultimately, of formula (IV), this route can be employed to provide stereospecific compounds of formula (I).

Compounds of formula (V) are prepared from the allyl alcohol

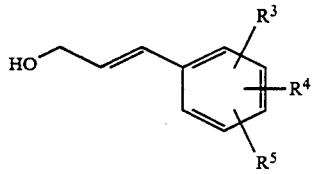

(VI)

using as epoxidising agent a reagent such as titanium isopropoxide-t-butyl peroxide in the presence of L or D diethyl tartrate which yields the S,S or R,R epoxide with the above E olefin. When the Z olefin is used as starting material, the appropriate S,R and R,S stereosisomers result. Compounds of formula (VI) can be prepared from the appropriate benzaldehyde via a sequence of reactions involving reaction with malonic acid to provide the cinnamic acid derivative, treatment with oxalyl chloride to give the acid chloride, and reduction with a reagent such as lithium tri-t-butoxyaluminohydride.

Compounds of formula (I) in which $R^1$ is alkyl, that is, a saturated group can be prepared preferably by hydrogenation of the appropriate compound in which $R^1$ is alkenyl or alkynyl, with, for example, hydrogen and a heavy metal catalyst such as $PtO_2$ or Pd/carbon or other catalytic systems, preferably at a temperature of from 0° C. to 100° C. and in an inert organic solvent such as for example ethanol.

The following scheme gives examples of the way in which preferred compounds of the invention may be prepared:

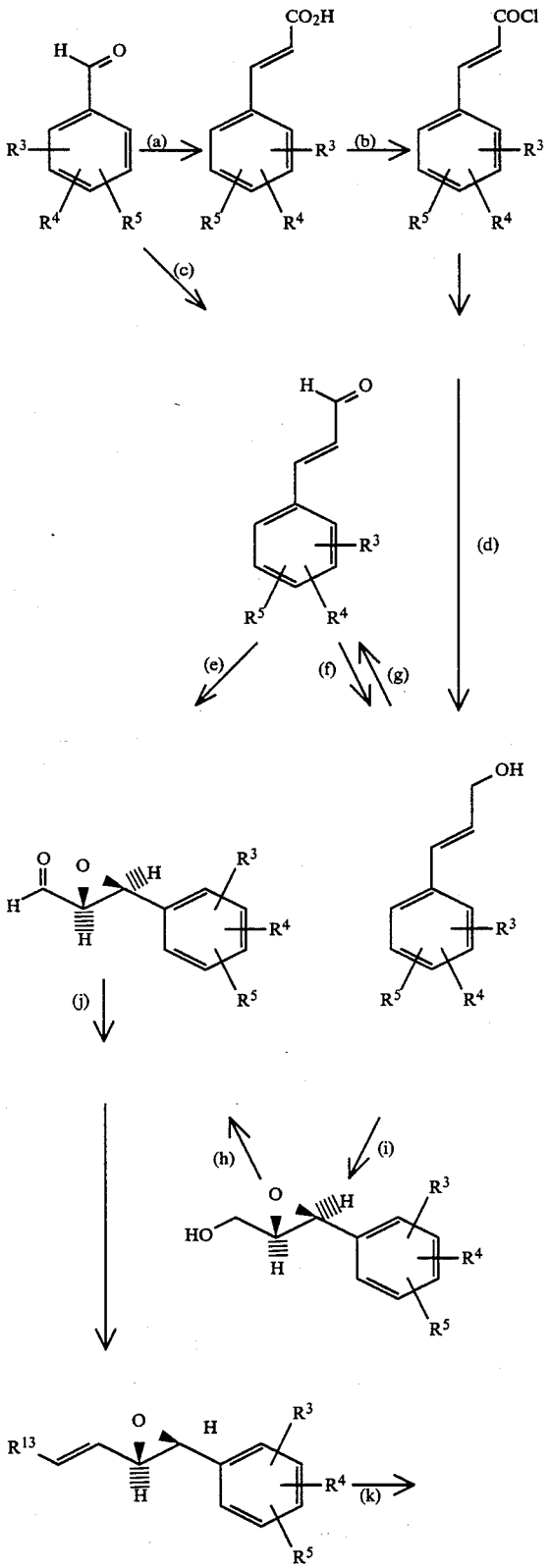

-continued

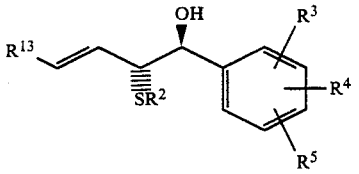

Key:
(a) reaction with malonic acid in pyridine and piperidine.
(b) reaction with oxalyl chloride in ether
(c) reaction with formylmethylenetriphenylphosphorane in toluene
(d) reaction with lithium tri-t-butoxyaluminohydride in tetrahydrofuran
(e) reaction with hydrogen peroxide and sodium hydrogen carbonate in methanolic solution
(f) reaction with sodium borohydride in methanol
(g) reaction with manganese dioxide in dichloromethane
(h) reaction with chromium oxide in pyridine
(i) reaction with titanium isopropoxide-t-butyl peroxide in dichloromethane and L-diethyl tartrate
(j) reaction with $R^{13}CH_2P^{\oplus}Ph_3Br^{\ominus}$ in the presence of butyl lithium and in tetrahydrofuran as solvent
(k) reaction with $R^2SH$ in methanol.

The compounds of the present invention are pharmacologically active, being leukotriene antagonists as shown by the in vitro test on guinea pig ileum segments at concentrations of from 10 ng to 50 $\mu$g, according to the method of Schild (1947) Brit. J. Pharm. 2, 197–206 (the unprotected compounds of formula (I) described in the following Examples exhibited an $IC_{50}$ against $LTD_4$ of less than $10^{-5}$ molar). Also compounds of the invention are active in the in vivo Guinea Pig Pulmonary Function Test of Austin and Drazen (1974) J. Clin. Invest. 53 1679–1685 at intravenous dosage levels of from 0.05 $\mu$g to 5.0 mg/kg and in a modified "Herxheimer" test (Journal of Physiology (London) 117 251 (1952)) at doses of from 25 to 200 mg/kg. The "Herxheimer" test is based on an $LTD^4$— induced bronchospasm in guinea pigs which closely resembles an asthmatic attack in man.

The compounds are accordingly indicated for therapeutic use in the treatment of diseases in which leukotrienes are implicated. These include allergic reactions of the pulmonary system in which leukotrienes are thought to be casual mediators of bronchospasm, for example, in allergic lung disorders such as extrinsic asthma and industrial asthmas such as Farmers lung and Pigeon Fanciers lung, and in other inflammatory disorders, for example, associated with acute or chronic infections diseases such as allergic skin diseases, ectopic and atopic eczemas, psoriasis, contact hypersensitivity and angioneurotic oedema, bronchitis and crystic fibrosis and rheumatic fever.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for examples by the oral or rectal route, topically or parenterally, for example by injection, and especially by inhalation, being usually employed in the form of a pharmaceutical composition. Such compositions are prepared in a manner well known in the pharmaceutical art and normally comprises at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages from human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by I.R. and/or n.m.r. and/or mass spectra and the purity of the product was checked in most cases by HPLC. The involatile products were examined by mass spectrometry using the fast atom bombardment (FAB) technique in the negative ion mode. Significant $[M—H]^-$ions (and characteristic fragment ions) were observed.

EXAMPLE 1

(a) 3-Carboxycinnamaldehyde, methyl ester

3-Carboxybenzaldehyde methyl ester (16.4 g) was dissolved in toluene (125 ml) and crystalline formylmethylene triphenylphosphorane (30.4 g) added with stirring under nitrogen. The mixture was brought to 100° C. and stirred for 4–5 hours. The dark straw coloured solution was evaporated in vacuo and the residue extracted with diethyl ether. The insoluble triphenylphosphine oxide was removed by filtration and the dark yellow filtrate was concentrated in vacuo and chromatographed on silica gel using diethylether/n-hexane 50/50 v/v as developing solvent. The required compound was obtained as a pale yellow crystalline solid. m.p. 86°–87° C.

(b) 3-(2-Formyl-1,2-oxido-ethyl)benzoic acid, methyl ester

3-Carboxycinnamaldehyde methyl ester (400 mg) was dissolved in methanol (12 ml) and added dropwise to a stirred solution of sodium bicarbonate (640 mg) and 28% hydrogen peroxide (1.6 ml) in water (24 ml). After the addition was complete the mixture was stirred for 1½ hours at room temperature. At this point TLC showed absence of starting aldehyde. The hazy solution was extracted via dichlormethane (3×10 ml) and evaporated in vacuo to give a nearly colourless oil (453 mg) mainly as the required aldehyde hydrate. Azeotropic distillation of this product from benzene led to the title compound as a nearly colourless oil (340 mg) which readily crystallised on storage in the freezer.

(c) 3-(4-Formyl-1,2-oxido-but-3(E)-enyl)benzoic acid, methyl ester

The product of (b) was dissolved in benzene (40 ml) and crystalline formylmethylenetriphenylphosphorane (2 g) was added and the mixture stirred at room temperature under nitrogen for 2 hours. The benzene was evaporated in vacuo and the residue extracted via diethylether to remove insoluble triphenylphosphine oxide. The ether extract was evaporated and the residue dissolved in a little diethylether/n-hexane, 50/50 v/v, and chromatographed on silica gel using the same solvent mixture for development. The fractions containing the title compound were bulked and evaporated to give the compound as a pale yellow oil.

(d) 3-(1,2-Oxido-pentadeca-3(E),5(Z)-dienyl)benzoic acid, methyl ester n-Decyltriphenylphosphonium bromide (2.45 g) was dissolved in dry tetrahydrofuran (50 ml), stirred under nitrogen and cooled to −78° C. Butyl lithium (1.55M solution in hexane, 3.4 ml) was added gradually with immediate formation of and orange yellow colour. After 15 minutes a solution of the product from (c) in tetrahydrofuran (5 ml) was added rapidly and the solution kept at −78° C. for 20 minutes, then allowed to come slowly to room temperature. The solution was evaporated in vacuo and the residue extracted with diethylether/n-hexane 50/50 v/v. The solvent extract was concentrated and chromatographed on silica gel using the same solvent mixture for development. The title compound was obtained as a colourless oil crystallizing on refrigeration.

(e) Rel(1R,2S)-3-(2-S-cysteinyl-1-hydroxypentadeca-3(E),5(Z)-dienyl)benzoic acid The compound from (d) was reacted under nitrogen with a solution of N-trifluoroacetylcysteine methyl ester (0.88 g) and triethylamine (1.1 ml) in dry methanol (4.5 ml) at room temperature for 24 hours. After this time the bulk of the starting epoxide had disappeared as indicated by TLC.

The solution was evaporated in vacuo, then dissolved in a little diethylether/n-hexane 50/50 v/v and chromatographed on silica gel developing at first with the same solvent mixture to remove trace amounts of the starting epoxide, then with diethylether to give the fully protected version of the title compound as a very pale straw coloured oil. The product was dissolved in tetrahydrofuran (7 ml) and lithium hydroxide solution (1M, 8 ml) added, followed by additional water to give a hazy solution. After 3 days the hydrolysis was incomplete, and further lithium hydroxide solution (4 ml) was added. After further 4 days the clear solution at pH ca 11 was extracted with diethylether. The residual aqueous phase was then carefully adjusted to pH 3.5–4 (dilute hydrochloric acid) then extracted several times with dichloromethane/methanol (3/1 v/v). The bulked organic phase was carefully evaporated in vacuo to give the title compound initially a pale straw coloured oil which gradually turned to a brittle solid.

The following compound was similarly prepared. Rel-(1R,2S)-3-(2-S-cysteinylglycinyl-1-hydroxypentedeca-3(E),5(Z)-dienyl)benzoic acid obtained as a light straw coloured oil.

EXAMPLE 2

(A) 3-Methoxycarbonylcinnamic acid

3-Carboxybenzaldehyde methyl ester (82 g) was dissolved in dry pyridine (250 ml) and malonic acid (52 g) added to the stirred solution. Piperidine (5 ml) was then added and the solution slowly heated to reflux. There was a slightly exothermic reaction accompanied by the evolution of carbon dioxide. After refluxing the solution for 1 hour an additional portion of malonic acid (25.1 g) was added. The solution was then refluxed for a further 30 minutes before being cooled and added to ice and 5M hydrochloric acid (1 liter). The resultant white solid was filtered off and washed with water before being dried in vacuo at 50° C. for 2 days. The crude product was then recrystallized from glacial acetic acid to give colourless plates, m.p. 189°–190° C. exclusively the E isomer.

(b) (E)-3-Methoxycarbonylcinnamyl chloride

Oxalyl chloride (13.9 g) was added to a stirred suspension of 3-methoxycarbonylcinnamic acid (20.6 g) in dry ether (200 ml) and then 1 drop of DMF was added to catalyse the reaction. After being stirred for 1 hour at room temperature all the solid and dissolved and the solution was evaporated to dryness to yield the white crystalline acid chloride m.p. 70°–71° C.

(c) (E)-3-Methoxycarbonylcinnamyl alcohol

3-Methoxycarbonylcinnamyl chloride (24 g) was dissolved in dry tetrahedrofuran and then this solution added to lithium tri-tert-butoxyaluminohydride (63.5 g) dissolved in tetrahydrofuran (250 ml) at −78° C. The resultant clear solution was stirred at −78° C. for 30 minutes then it was added to ice and 2M hydrochloric acid (750 ml). The two phase mixtures was extracted 4 times with dichloromethane. After drying the dichloromethane was evaporated to yield the title compound as a pale yellow oil.

(d) (E)-3-(3-Hydroxy-1,2-oxidopropyl)benzoic acid methyl ester

3-Methoxycarbonylcinnamyl alcohol (1.92 g) was dissolved in dichloromethane (50 ml), cooled to 0° C. and metachloroperoxybenzoic acid (1.72 g) in dichloromethane 10 ml was added to the cooled solution dropwise. The temperature of the reaction mixture was then allowed to rise to room temperature. After 2 hours the meta-chlorobenzoic acid was filtered off and the solution washed with saturated sodium bicarbonate solution twice. After drying evaporation of the dichloromethane layer yielded the title compound as a colourless oil.

(e) (Alternative Method)

(1S,2S) 3-(3-Hydroxy-1,2-oxidopropyl)benzoic acid, methyl ester

Titanium tetra-isopropoxide (1.3 ml) was dissolved in dry dichloromethane (12 ml) and the stirred solution cooled to −60 ° C. L-Diethyl tartrate, (6.0 mM) was then added and the solution allowed to warm to −20° C. and stirred for a further 10 minutes. 3-Methoxycarbonylcinnamyl alcohol (960 mg) was then added. Finally a 3M solution of tert-butyl hydroperoxide (6 ml) in 1,2-dichloroethane was added and the solution stored at −18° C. for 16 hours. Ether (15 ml) was then added to the reaction mixture followed by a saturated solution of aqueous sodium sulphate (2 ml). The mixture was stirred at room temperature for 1 hour and filtered through celite. Toluene (100 ml) was added to the solution and it was evaporated to afford a colourless oil which was chromatographed on a silica column eluted with ether. The diethyl tartrate eluted first followed by the title compound which was obtained after evaporation of solvent as a colourless oil.

(f) 3-(2-Formyl-1,2-oxidoethyl)benzoic acid, methyl ester

Chromium trioxide (2.5 g) was added to a solution of pyridine (3.9 g) in dichloromethane (100 ml) at 7° C. The temperature of the stirred solution was allowed to rise to 14° C. and 3(3-hydroxy-1,2-oxidopropyl)benzoic acid methyl ester (1.04 g) was added in dichloromethane (2 ml). The solution darkened and a black oil came out of solution. After 30 minutes at 22° C. the dichloromethane layer was decanted off and filtered through Fluorosil. Upon evaporation this solution yielded the title compound as a colourless oil.

(g) Rel (1R,2S)-3-(2-S-cysteinyl-1-hydroxypentadeca-3(E),5(Z)-dienyl)benzoic acid The above compound was prepared from the compound of step (f) above by the process described in steps (c), (d) and (e) of Example 1.

EXAMPLE 3

(a) Rel (1R,2S)-3-[2-(2-carboxyethylthio)-1-hydroxypentadec-3(E),5(Z)-dienyl]benzoic acid dimethyl ester Methyl 3-mercaptopropionate (240 mg) was dissolved in dry methanol (3 ml). Triethylamine (250 μl) was then added and the resultant solution added to 3-(1,2-oxidopentadeca-3(E),5(Z)-dienyl)benzoic acid methyl ester (712 mg). The resultant clear solution was then stored at 40° C. for 16 hours after which time it was evaporated to dryness and chromatographed on a silica column eluted with ether. The title compound was obtained as a colourless oil.

(b) Rel (1R,2S)-3-[2-(2-carboxyethylthio)-1-hydroxypentadec-3-(E),5(Z)-dienyl]benzoic acid Rel (1R,2S)-3[2-(2-carboxyethylthio)-1-hydroxypentadec-3(E),5(Z)-dienyl]benzoic acid dimethyl ester (476 mg) was dissolved in tetrahydrofuran (10 ml) and a 1M lithium hydroxide solution (3 ml) was added to it. The mixture was then stirred at room temperature for 2 days, the pH of the solution was then adjusted to 4 using dilute hydrochloric acid. Finally this solution was extracted four times with dichloromethane which, after drying ($MgSO_4$) and evaporation, yielded the title compound as an off-white solid, m.p. 87°–90° C.

EXAMPLE 4

(a) (1S,2S)-3-(1,2-Oxidopentadeca-3-(E),5(Z)-dienyl)-benzoic acid

The above compound was prepared from the product of Example 2(e) by the processes described in Examples 2(f), 1(c) and 1(d). MS M+356.

(b) (1S,2R)-3-[2-(2-Carboxyethylthio)-1-hydroxy-pentadeca-3(E),5(Z)-dienyl]benzoic acid, dimethyl ester The chiral epoxide prepared as described in step (a) was reacted by the process described in Example 3(a) to give the little compound as a pale oil. MS (FAB)M+477

(c) (1S,2R)-3-[2-(2-Carboxyethylthio)-1-hydroxy-pentadeca-3(E),5(Z)-dienyl]benzoic acid The diester was hydrolysed by the method described in Example 3(b) to give the title compound as a white solid, m.p. ca 50° C., $[\alpha]_D+50.1°$ (c=2.3, MeOH), MS (FAB) [M—H]−447

EXAMPLE 5

(1R,2S)-3-[2-(2-Carboxyethylthio)-1-hydroxy-pentadeca-3(E),5(Z)-dienyl]benzoic acid 1R,2R)-3-(3-Hydroxy-1,2-oxidopropyl)benzoic acid, methyl ester was prepared by the method described in Example 2(e) using D(−) diethyl tartrate in place in the L(+) isomer. This epoxide was then reacted by the processes described in Examples 2(f), 1(c), 1(d), 3(a) and 3(b) to give the title compound as a pale oil.

EXAMPLE 6

(a) (E)-2-Methoxycaronylcinnamyl alcohol

2-Methoxycarbonylcinnamic acid, m.p. 176° C., was prepared by the method described in Example 2(a) and converted to the acid chloride, m.p. 75°-80° C., by the method described in Example 2(b). A solution of this acid chloride (15.5 g) in ether (250 ml) was added to a stirred suspension of sodium borohydride on alumina (60 g—prepared by addition of a solution of 1 part of sodium borohydride in 2 parts of water to 10 parts of alumina, with cooling, followed by drying under vacuum) in ether (360 ml). The mixture was stirred for 2 hours at room temperature and filtered. The filtrate was washed with 10% sodium carbonate solution, then with saturated sodium chloride solution, dried and evaporated to yield the title compound as a colourless oil.

(b) (E)-2-(3-Hydroxy-1,2-oxidopropyl)benzoic acid, methyl ester

Oxidation of (E)-2-methoxycarbonylcinnamyl alcohol with meta-chloroperoxybenzoic acid as described in Example 2(d) followed by chromatography of the crude product on a silica column eluted with 2:1 ether:-hexane gave the title compound as a pale oil.

(c) 3-[1-(2-Methoxycarbonylethylthio)-tetradec-2(E),4(Z)-dienyl]-1,3-dihydro-isobenzofuran-1-one 2-(4-Formyl-1,2-oxidobut-3(E)-enyl)benzoic acid methyl ester, m.p. <50° C. was prepared from the compound of step (b) above by the processes described in Examples 2(d), 2(f) and 1(c). Further reaction of this compound by the methods described in Examples 1(d) and 3(a) gave as the major product the lactone title compound.

(d) Rel (1R,2S)-2-[2-(2-Carboxyethylthio)-1-hydroxypentadeca-3(E),5(Z)-dienyl]benzoic acid, disodium salt A solution of 3-[1-(2-methoxycarbonylethylthio)-tetradeca-2(E),4(Z)-dienyl]-1,3-dihydro-isobenzofuran-1-one (115 mg) in tetrahydrofuran (1 ml) and 0.5M sodium hydroxide solution (0.96 ml) was stirred at room temperature for 16 hours. The solution was evaporated and the residue was washed with ether to leave the title compound as a viscous gum.

EXAMPLE 7

(a) 9-Bromo-2-methyl-4-decene n-Butyl lithium (1.5M solution in hexane 6.8 ml) was added to a stirred suspension of (3-methylbutyl)-triphenylphosphonium bromide (4.1 g) in dry tetrahydrofuran (50 ml) at −60° C. under nitrogen. The dark mixture was stirred for 40 minutes at −70° C. then a solution of 6-bromohexanal (1.8 g) in dry tetrahydrofuran (6 ml) was added. The pale mixture was stirred for a further 1 hour at −70° C. then evaporated under vacuum. The residue was extracted with ether and the extract was evaporated to a pale oil which was chromatographed on silica gel, eluting with 1:1 ether:hexane, to give the title compound as a colourless oil. MS M+232/234.

(b) (9-Methyl-6-decenyl)-triphenylphosphonium bromide

A solution of 9-bromo-2-methyl-4-decene (0.9 g) and triphenylphosphine (1.5 g) in xylene (50 ml) was heated under reflux for 4 days. The mixture was cooled, the supernatant was decanted and the residue was washed with ether and dried under vacuum to give the title compound as a pale gum.

(c) (1S,2S)-3-(4-Formyl-1,2-oxidobut-3(E)-enyl)benzoic acid methyl ester

This compound was prepared from the product of Example 2(e) by the process described in Examples 2(f) and 1(c).

(d) (1S,2R)-3-[2-(2-Carboxyethylthio)-1-hydroxy-14-methylpentadeca-3(E),5(Z),11(Z)-trienyl]benzoic acid The above compound was prepared from the compounds of steps (b) and (c) above by the processes described in Examples 1(d), 3(a) and 3(b). MS (FAB) [M—H] 459

EXAMPLE 8

(A) 1-Bromo-9-methyldecane

A solution of 9-bromo-2-methyl-4-decane (1.0 g) in ethanol (40 ml) was hydrogenated for 20 minutes at 60 p.s.i. over platinum oxide (10 mg). The catalyst was filtered off and the filtrate was evaporated to give the title compound as a pale oil.

(b) (9-Methyldecyl)-triphenylphosphorium bromide

A solution of 1-bromo-9-methyldecane (1.0 g) and triphenylphosphine (1.7 g) in xylene (50 ml) was heated under reflux for 24 hours. The mixture was cooled, the supernatant was decanted and the residue was washed with ether and further dried by addition of benzene and evaporation to give the title compound as a pale gum.

(c) (1S,2R)-3-[2-(2-Carboxyethylthio)-1-hydroxyl-14-methylpentadeca-3(E),5(Z)-dienyl]benzoic acid The above compound was prepared from the compound of step (b) above and (1S,2S)-3-(4-formyl-1,2-oxidobut-3(E)-enyl) benzoic acid methyl ester (Example 7(c)) by the processes described in Examples 1(d), 3(a) and 3(b). MS (FAB) [M—]−461

EXAMPLE 9

(1S,2R)-3-[2-(2-Aminocarbonylethylthio)-1-hydroxypentadeca-3(E),5(E)-dienyl]benzamide A solution of (1S,2R)-3-[2-(2-carboxyethylthio)-1-hydroxypentadeca-3(E),5(Z)-dienyl]benzoic acid, dimethyl ester (50 mg) in methanolic ammonia solution (2 ml) was stored at 50° C. in a sealed bottle for 3 weeks. The brown solution was evaporated and the residue was purified by preparative reverse phase HPLC to give the title compound as a pale solid, m.p. 83°-84° C. MS (FAB) [M—H]−445.

EXAMPLE 10

(a) 3-Cyanocinnamic acid

3-Cyanobenzaldehyde was reacted with malonic acid by the method described in Example 2(a) to give the title product, m.p. ca 240° C.

(b) 3-Aminocarbonylcinnamic acid

A solution of 3-carboxymethylcinnamic acid (427 g) (Example 2(a)) in dimethyl formamide (4.25 l) and aqueous ammonia (specific gravity 0.88, 8.5 l) was stored at room temperature for 4 days, concentrated to call 11 l, and then treated with ice (8 kg) and concentrated hydrochloric acid (1 l). The precipitated title product was washed with water and dried, m.p. >260° C.

(c) 3-Cyanocinnamic acid (Alternative method)

Phosphorus oxychloride (746 ml) was added to a stirred suspension of 3-aminocarbonylcinnamic acid (765 g) in dimethyl formamide (7.65 l). The resulting solution was heated at 70°-80° C. for 50 minutes, cooled to 50°-60° C., and poured onto ice (40 l) to precipitate the title compound which was washed with water and dried, m.p. 242° C.

(d) 3-Cyanocinnamyl alcohol

The acid of steps (a) and (c) above was convered to the alcohol by the process described in Example 6(a) giving the title compound as a low melting white solid.

(e) (1S,2R)-3-[2-(2-Carboxyethylthio)-1-hydroxy-pentadeca-3(E),5(Z)-dienyl]benzonitrile, methyl ester The above compound was prepared from the compound of step (d) above by the process described in Examples 2(e), 2(f), 1(c), 1(d) and 3(a).

(f) (1S,2R)-3-[2-(2-Carboxyethylthio)-1-hydroxypentadeca-3(E),5(Z)-dienyl]benzonitrile A solution of the methyl ester (step (e)) (950 mg) in methanol (200 ml) and 0.2M potassium carbonate solution (95 ml) was stirred at room temperature for 16 hours, concentrated to 70 ml, diluted with water (50 ml) and washed with ether (50 ml). The aqueous phase was acidified to pH3 and extracted with dichloromethane (3×50 ml). The extract was dried and evaporated to give the title product as a pale gum. MS(FAB) [M—H] 428.

EXAMPLE 11

(1S,2R)-5-{3-[2-(2-Carboxyethylthio)-1-hydroxy-pentadeca-3(E),5(Z) dienyl]phenyl}-1H-tetrazole A stirred suspension of ammonium chloride (5 g) and sodium azide (5 g) in a solution of (1S,2R)-3-[2-(2-carboxyethylthio)-1-hydroxy-pentadeca-3(E),5(Z)-dienyl]-benzonitrile (Example 10, 780 mg) in dimethyl formamide (25 ml) was heated at 100°-105° C. for 12 hours. The dark mixture was filtered and the filtrate was diluted with M hydrochloric acid (250 ml) and extracted with dichloromethane (3×150 ml). The extract was washed with water, dried and evaporated to give a dark oil containing the 3(E),5(Z) and 3(E),5(E) isomers in the ratio 30:70. The isomers were separated by preparative reverse phase HPLC to give the title compound as a crisp solid.

EXAMPLE 12

(a) (1S,2R)-5-{3-[2-(2-Carboxyethylthio)-1-hydroxypentadeca-3(E),5(E)-dienyl]phenyl}-1H-tetrazole The above compound was separated from the reaction described in Example 11. MS(FAB) [M—H]−471.

(b) (1S,2R)-5-3-[2-(2-Carboxyethylthio)-1-hydroxypentadeca-3(E),5(E)-dienyl]phenyl}-1H-tetrazole, sodium salt.

A solution of the product of (a) (273 mg) was dissolved in 0.5M sodium bicarbonate solution (1.16 ml) and the solution was freeze dried to give the title compound as a pale solid.

EXAMPLE 13

(1S,2R)-3-[2-(2-Carboxyethylsulphinyl)-1-hydropentadeca-3(E),5(Z)-dienyl]benzoic acid 0.5M Sodium periodate solution (1.8 ml) was added to a stirred solution of (1S,2R)-3-[2-(2-carboxyethylthio)-1-hydroxypentadeca-3(E),5(Z)-dienyl]benzoic acid (372 mg) in 0.5M sodium bicarbonate solution (3.2 ml) and methanol (3.2 ml) at 0°-5° C. The mixture was stirred for 1.5 hours at 0°-5° C. then further 0.5M sodium periodate solution (0.36 ml) was added. The mixture was stirred for a further 3 hours at 0°-5° C. then diluted with water, acidified to pH3 and extracted with 3:1 dichloromethane:methanol. The extract was dried and evaporated to give the title compound as a crisp solid shown by reverse phase HPLC and nmr studies to contain two diastereoisomeric sulphoxides in the ratio 2:1. MS(FAB) [M—H−463

EXAMPLE 14

(1S,2R)-5-{3-[2-(2-Carboxyethylsulphinyl)-1-hydroxypentadeca-3(E),5(E)dienyl]phenyl}1H-tetrazole The above compound was prepared from (1S,2R)-5-{3-[2-(2-carboxyethylthio)-1-hydroxypentadeca-3(E),-5(E)-dienyl]phenyl}-1H-tetrazole by the process described in Example 13. The two diastereoisomers were separated by preparative reverse phase HPLC. MS (FAB) [M—H]−487

EXAMPLE 15

(1S,2R)-5-{3-[2-(2-Carboxyethylsulphonyl)-1-hydroxypentadeca-3(E),5(E)-dienyl]phenyl}-1H-tetrazole A solution of potassium persulphate (150 mg) in water (0.5 ml) was added to a stirred solution of (1S,2R)-5-{3-[2-(2-carboxyethylthio)-1-hydroxypentadeca-3(E),5(E)-dienyl]phenyl}-1H-tetrazole (50 mg) in 0.5M sodium bicarbonate solution (2 ml) and methanol (1 ml) at 0°-5° C. The mixture was stirred for 4 hours at 0°-5° C., diluted with water, acidified and extracted with 3:1 dichloromethane:methanol. The extract was dried and evaporated to give the title compound as a crisp solid. MS (FAB) [M—]−503.

EXAMPLES 16 AND 17

(1S,2R)-3-{2-(1H-Tetrazol-5-yl)ethylthio]-1-hydroxypentadeca-3(E),5(E)-dienyl}benzoic acid and 3(E),5(Z) isomer (1S,2S)-3(1,2-Oxidopentadeca-3(E),5(Z)-dienyl)benzoic acid, methyl ester (1.78 g) prepared as in Example 4(a) was dissolved in a solution of 3-thiopropionitrile (0.44 g) in methanol (5 ml) and triethylamine (0.5 ml) under nitrogen. This clear solution was allowed to stand at room temperature for 6 hours and then evaporated to dryness. The resultant pale yellow oil was chromatographed on a silica column eluted with ether/hexane 50/50. The required product (1S,2R)-3-{2-[2-cyanoethylthio]-1-hydroxypentadeca-3(E),5(Z)-dienyl}benzoic acid methyl ester (1.39 g) was obtained as a colourless oil.

This ester (1.25 g) was dissolved in tetrahydrofuran (10 ml) and 1M aqueous lithium hydroxide solution (3 ml) added. This solution was then stirred overnight at room temperature under nitrogen. At the end of this period further 1M aqueous lithium hydroxide solution (2 ml) was added and the solution warmed to 30° C. for 3 hours. The solution was then evaporated to remove the tetrahydrofuran and the remaining aqueous solution was adjusted to a pH of 3 with 2M hydrochloric acid. This solution was then extracted 3 times with ether and the combined ether extracts dried ($Mg_2SO_4$) and evaporated to an almost colourless oil which slowly crystallized at 0° C. to yield (1S,2R)-3-{2-[2-cyanoethyl]-1-hydroxypentadeca-3(E),5(Z)-dienyl}benzoic acid. This free acid (500 mg) was dissolved in dimethylformamide (10 ml), sodium azide (2 g) and ammonium chloride (2 g) were added and the stirred suspension heated to 120° C. for 5.5 hours. At the end of that period the mixture was diluted with water (30 ml) and the pH of the solution adjusted to 3 with dilute hydrochloric acid prior to extraction five times with ether. The ether extracts were dried ($Mg_2SO_4$) and evaporated to a brown oil. The oil was dissolved in a mixture of methanol:water (85:15) and applied to a preparative reverse phase HPLC column which was eluted with methanol:water (85:15) containing 0.5% acetic acid. The 3(E),5(Z) isomer of (1S,2R)-3-{2-[2-1H-tetrazol-5-yl)ethylthio]-1-hydroxypentadecadienyl}benzoic acid eluted first followed closely by the more abundant 3(E),5(E) isomer.

EXAMPLES 18–25

The compounds shown in the Table below were prepared using the processes described in Example 3 with the appropriate thiols.

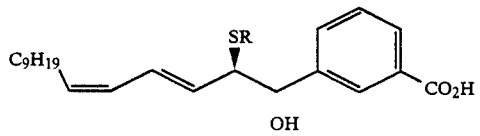

| R |
|---|
| $CH_2CO_2H$ |
| $CH(CH_3)CO_2H$ |
| $CH(CH_3)CH_2CO_2H$ |
| $CH_2CH(CH_3)CO_2H$ |
| $(CH_2)_3CO_2H$ |
| $(CH_2)_5CO_2H$ |
| $CH(CH_3)CONHCH_2CO_2H$ |
| $(CH_2)_2CN$ |

EXAMPLE 26

(a) 3-(1,2-Oxidopentadeca-3(Z)-enyl)benzoic acid, Methyl ester n-Butyl lithium (1.5M solution in hexane, 3.3 ml) was added dropwise to a stirred solution of dodecyltriphenyl phosphonium bromide (2.66 g) in dry tetrahydrofuran (50 ml) at −70° C. under nitrogen. The deep orange solution was stirred for 10 minutes at −70° C. then a solution of 3-(2-formyl-1,2-oxidoethyl)benzoic acid, methyl ester (Example 1(b), 1.03 g) in tetrahydrofuran (5 ml) was added. The pale suspension was allowed to warm to room temperature, and evaporated and the residue was extracted with 1:1 ether:hexane. The extract was evaporated and the residue chromatographed on silica gel eluting with 1:1 ether:hexane. The title compound was obtained as a colourless oil which solidified on cooling.

(b) Rel (1R,2S)-3-[2-(2-Carboxyethylthio)-1-hydroxypentadeca-3(Z)-enyl]benzoic acid The above compound was prepared from the product of step (a) by the process described in Example 3.

EXAMPLES 27 AND 28

Rel (1R,2S)-3-[2-(2-Carboxyethylthio)-1-hydroxyundeca-3(E),5(Z)-dienyl]benzoic acid and Rel (1R,2S)-3-[2-(2-carboxyethylthio)-1-hydroxynonadeca-3(E),5(Z)-dienyl]benzoic acid The above compounds were prepared from the appropriate phosphonium bromides by the processes described in Examples 1(d), 3(a) and 3(b).

EXAMPLE 29

(a) (8-Tetrahydropyranyloxyoctyl)triphenylphosphonium bromide

A solution of 1-bromo-8-tetrahydropyranyloxyoctane (9.8 g) and triphenyl phosphine (8.8 g) in acetonitrile (50 ml) was heated under reflux for 8 hours. The solution was evaporated and the residue washed with ether to give the title compound as a hygroscopic white solid which was dried by addition of benzene and re-evaporation.

(b) 2-(11-Phenyl-8-undecenyloxy)-tetrahydropyran n-Butyl lithium (1.6M solution in hexane, 20 ml) was added to a stirred solution of the product of step (a) (11.0 g) in dry tetrahydrofuran at −70° C. under nitrogen. The orange solution was stirred for 30 minutes at −70° C. then a solution of 3-phenyl-propionaldehyde (2.75 g) in tetrahydrofuran (7 ml) was added. The pale solution was allowed to warm to room temperature and then evaporated. The residue was extracted with ether and the extract again evaporated and the residue was chromatographed on silica-gel eluting with 1:1 ether:-hexane to give the title compound as a pale oil.

(c) 11-Phenyl-8-undecenol

A solution of the product of step (b) (8.7 g) in tetrahydrofuran (150 ml) of 2M hydrochloric acid was stirred at room temperature for 4 hours. The mixture was neutralised with sodium bicarbonate solution and extracted with dichloromethane. Evaporation of the extract and chromatography of the residue on silica gel eluting with 1:1 ether:hexane to remove starting material, then with ether, gave the title product as a pale oil.

(d) 11-Phenyl-8-undecenol tosylate

4-Toluenesulphonyl chloride (1.3 g) was added in portions to a stirred solution of the product of step (c) (1.5 g) in pyridine at 0°–5° C. The mixture was stirred for 16 hours at 0°–5° C. then poured onto ice-hydrochloric acid and extracted with ether. The extract was washed with sodium bicarbonate and sodium chloride solutions, dried and evaporated to give the title compound as a pale oil.

(1S,2S)-3-(1,2-Oxido-16-phenylhexadeca-3(E),5(Z),13(Z)-trienyl)benzoic acid, methyl ester A solution of the product of step (d) (1.9 g) and triphenyl phosphine (1.3 g) in acetonitrile (20 ml) was heated under reflux for 48 hours. The solution was evaporated and the residue was washed with ether and further dried by addition of benzene and re-evaporation to leave the crude phosphonium salt as a semi-solid mass.

n-Butyl lithium (1.6M solution in hexane, 1.5 ml) was added to a stirred solution of this phosphonium salt in dry tetrahydrofuran (50 ml) at −70° C. under nitrogen. The deep yellow solution was stirred for 30 minutes at −70° C. then a solution of (1S,2S)-3-(4-formyl-1,2-oxidobut-3(E)-enyl)benzoic acid, methyl ester (Example 7(c)) (0.5 g) in tetrahydrofuran was added. The mixture was allowed to warm to room temperature, evaporated and the residue was extracted with 4:1 ether:dichloromethane. The extract was again evaporated and the residue was chromatographed on silica gel eluting with 1:1 ether:hexane to give the title compound as a pale oil.

(f) (1S,2R)-3-[2-(2-Carboxyethylthio)-1-hydroxy-16-phenylhexadeca-3(E),5(Z),13(Z)-trienyl]benzoic acid The above compound was prepared from the product of step (e) by the processes described in Example 3.

EXAMPLE 30

(a) 11-Phenyl-undecanol

A solution of 11-phenyl-8-undecenol (Example 29(c), 2.9 g) in ethanol (300 ml) was hydrogenated at 60 p.s.i. over 10% palladium on charcoal (0.6 g) for 1 hour. The catalyst was filtered off and the filtrate was evaporated to give the title compound as a colourless oil.

(b) 11-Phenylundecanol tosylate

4-Toluenesulphonyl chloride (2.6 g) was added in portions to a stirred solution of the product of step (a) (2.9 g) in pyridine (10 ml) at 0° C. The solution was stirred for 16 hours at 0°-5° C. then poured onto ice-hydrochloric acid and extracted with ether. The extract was washed with sodium bicarbonate and sodium chloride solutions, dried and evaporated. The residue was chromatographed on silica gel eluting with 1:1 dichloromethane:hexane to give the title compound as a colourless oil.

(c) (1S,2R)-3-[2-(2-Carboxyethylthio)-1-hydroxy-16-phenylhexadeca-3(E),5(Z)-dienyl]benzoic acid The above compound was prepared from the product of step (b) by the process described in examples 29(e) and 3.

EXAMPLES 31 AND 32

(1S,2R)-3-[(2-S-Glutathionyl)-1-hydroxypentadeca-3(E),5(E)dienyl]benzoic acid and its 3(E),5(Z) isomer Glutathione (300 mg) was dissolved in a mixture of dry methanol (3 ml) and triethylamine (1 ml) and the solution added to (1S,2S)-3-(1,2-oxidopentadeca-3(E),5(Z)-dienyl]benzoic acid, methyl ester (prepared in Example 4(a)) under nitrogen. The resultant solution was allowed to stand at room temperature for 6 hours and the solvent then evaporated to dryness. Aqueous 2M lithium hydroxide solution (3 ml) was added and the solution stirred under nitrogen for 3 hours at room temperature. The pH of the solution was then adjusted to 4 with acetic acid and extracted with ether to remove non-polar impurities. The aqueous solution was extracted 5 times with chloroform:methanol 1:1. The combined extracts were evaporated to dryness to give a crude mixture of the title compounds which were separated on a preparative reverse phase HPLC column eluted with methanol:water 70:30 buffered with acetic acid and 0.88 ammonia to a pH of 5.3. The title compounds were pale yellow amorphous solids.

EXAMPLE 33

Rel (1R,2S)-3-(2-S-Cysteinyl-1-hydroxypentadeca-3(E),5(Z)-dienyl)benzoic acid, methyl ester A solution of 3-(1,2-oxidopentadeca-3-(E),5(Z)-dienyl)benzoic acid, methyl ester (Example 1(d), 0.5 g), N-trifluoroacetylcysteine methyl ester (0.4 g) and triethylamine (0.5 ml) in dry methanol (2.0 ml) was stored at room temperature for 3 days and then evaporated. The residue was chromatographed on silica gel, eluting first with 1:1 ether:hexane and then with ether to give the fully protected version of the title compound as a pale oil.

A solution of this compound (0.4 g) in methanol (7 ml) and 2M sodium carbonate solution (4 ml) was diluted with water to give a slight haziness and then stored at room temperature for 30 hours. The solution was diluted with water (20 ml), acidified to pH4 and extracted with dichloromethane (3×15 ml). The extract was evaporated and the residue was chromatographed on silica gel eluting with 1:1 dichloromethane:methanol to give the title compound as a pale oil.

EXAMPLE 34

(a) 3-(6-Formyl-1,2-oxidohexa-3(E),5(E)-dienyl)benzoic acid, methyl ester

A solution of 3-(2-formyl-1,2-oxido-ethyl)benzoic acid, methyl ester (Example 1(b), 0.7 g) in dichloromethane (10 ml) was added over 1 hour to a stirred solution of triphenylphosphoranylidene-crotonaldehyde (1.5 g) in dichloromethane (10 ml). The solution was stirred for a further 1.5 hours and then evaporated and the residue was extracted with ether. The extract was evaporated and the residue was chromatographed on silica gel, eluting with ether to give a pale yellow oil containing the title compound mixed with the 3(Z),5(E) isomer. A solution of this mixture (230 mg) and iodine (10 mg) in dichloromethane (20 ml) was stirred for 2 hours at room temperature and then evaporated. The residue was washed with hexane to remove iodine, leaving the title compound as a yellow oil.

(b) 3-(1,2-Oxidohexadeca-3(E),5(E),7(Z),10(Z)-tetraenyl)benzoic acid, methyl ester n-Butyl lithium (1.5M solution in hexane, 0.65 ml) was added slowly to a stirred solution of 3-(Z)-nonenyltriphenylphosphonium tosylate (0.56 g) in dry tetrahydrofuran (5 ml) at −70° C. The dark orange-brown solution was stirred for 10 minutes at −70° C. then a solution of the product of step (a) (210 mg) in tetrahydrofuran (2 ml) was added. The mixture was stirred for a further 15 minutes at 70° C., allowed to warm to room temperature and evaporated. The residue was chromatographed on silica gel eluting with 1:1 ether:hexane containing 1% triethylamine and further purified by HPLC to give the title compound as a pale oil.

(c) Rel (1R,2S)-3-[2-(2-Carboxyethylthio)-1-hydroxyhexadeca-3(E),5(E),7(Z),10(Z)-tetraenyl]benzoic acid, dimethyl ester A solution of the product of step (b) (3 mg), methyl 3-mercaptopropionate (2.4 μl) and triethylamine (5 μl) in dry methanol (100 μl) was stored at room temperature for 3 hours then the title compound was isolated by HPLC. MS M+486

(d) Rel (1R,2S)-3-[2-(2-carboxyethylthio)-1-hydroxyhexadeca-3(E),5(E),7(Z),10(Z)-tetracenyl]benzoic acid A solution of the product of step (c) (2.2 mg) is methanol and 0.5M potassium carbonate solution was stored at room temperature for 16 hours then the title compound was isolated by reverse phase HPLC.

EXAMPLE 35

(a) 3-Mercaptopropionamide

Methyl 3-mercaptopropionate (1.2 g) was dissolved in 0.88 ammonia (75 ml) and the solution stirred at 40° C. under nitrogen for 6 hours. The solution was then evaporated to dryness and the resultant white solid redissolved in dichloromethane this solution then being washed with 2M aqueous hydrochloric acid (10 ml) and dried ($Mg_2SO_4$). This solution upon evaporation yielded the title compound as white plates, m.p. 106° C., which were washed with ether.

(b) ((1S,2R),-3-[2-(2-Carbamylethylthio)-1-hydroxypentadeca-3(E),5(Z)-dienyl]benzoic acid, methyl ester 3-Mercaptopropioamide (12 mg) was dissolved in dry methanol (200 μl) under nitrogen and triethylamine (100 μl) added. This solution was then added to (1S,2S) 3(1,2-oxidopentadeca-3(E),5(Z)-dienyl)benzoic acid, methyl ester and the resultant solution allowed to stand at 40° C. for 3 hours. The solution was then evaporated to dryness and the residue chromatographed on a silica column eluted with ethyl acetate. The title compound was obtained as off white crystals, m.p. 65°–67° C.

(c) (1S,2R)-3-[2-(2-carbamylethylthio)-1-hydroxypentadeca-3(E),5(Z)-dienyl]benzoic acid A solution of the product of step (b)(40 mg) in tetrahydrofuran (2 ml) and M lithium hydroxide solution (0.2 ml) was stirred for 16 hours at room temperature. Further M lithium hydroxide solution (0.2 ml) was added and the solution was stirred for a further 24 hours then diluted with water, acidified to pH 3 and extracted with dichloromethane. The extract was dried and evaporated and the residue was further purified by preparative reverse phase HPLC to give the title compound.

EXAMPLE 36

Rel (1R,2S)-3-[2-(2-Carboxyethylthio-1-hydroxypentadeca-3(E),5(E)-dienyl]benzoic acid The product of Example 3(b) was shown by HPLC to contain about 10% of a second component. Isolation of this minor component by reverse phase HPLC on a $C_{18}$ Nucleosil column eluting with 80:20 methanol:water buffered to pH5.3 with acetic acid and ammonia gave the title compound as a crystalline solid.

EXAMPLE 37

(a) 3-Cyanocinnamaldehyde

A suspension of active manganese dioxide (20 g) in a solution of 3-cyanocinnamyl alcohol (Example 10(d), 4.0 g) in dichloromethane (100 ml) was stirred at room temperature for 16 hours. The mixture was filtered and the filtrate was evaporated to give the title product as a white solid, m.p. 100° C.

(b) 3(3-Cyanophenyl)-1,2-oxidopropanol

A solution of 3-cyanocinnamaldehyde (2.0 g) in methanol (20 ml) was added dropwise to a stirred solution of sodium bicarbonate (2.0 g) and 50% hydrogen peroxide (1.0 ml) in water (10 ml). The solution was stirred for 3 hours at room temperature then extracted with dichloromethane. The extract was dried and evaporated to give a colourless oil which was mainly the hemiacetal of the title aldehyde.

(c) 5-(3-Cyanophenyl)-4,5-oxido-2-pentenal

A mixture of the product of (b) and formylmethylenetriphenylphosphorane (3.0 g) in benzene (150 ml) was stirred at room temperature for 2 hours then filtered. The filtrate was evaporated and the residue was extracted with ether. The extract was again evaporated and the residue was chromatographed on silica gel eluting with 3:1 ether-hexane to give the title compound as a pale oil.

(d) Rel (1R,2S)-3-(1,2-Oxido-pentadeca-3(E),5(Z)-dienyl) benzonitrile

The above compound was prepared from the product of step (c) by the process described in Example 1(d).

(e) Rel (1R,2S)-3-[2-(2-Carboxyethylthio)-1-hydroxypentadeca3(E),5(Z)-dienyl]benzonitrile, melthyl ester The above compound was prepared from the product of step (d) by the process described in Example 3(a).

(f) Rel (1R,2S)-3-[2-(2-Carboxyethylthio)-1-hydroxypentadeca3(E),5(Z)-dienyl]benzonitrile The above compound was prepared from the product of step (e) by the process described in Example 3(b).

(g) Rel (1R,2S)-5-{3-[2-(2-Carboxyethylthio)-1-hydroxypentadeca3(E),5(Z)-dienyl]phenyl}-1H-tetrazole A mixture of the product of step (f) (100 mg), ammonium chloride (1.0 g) and sodium azide (1.0 g) in dimethylformamide (5 ml) was heated at 100° C. for 4 hours and then filtered. The filtrate was diluted with 2M hydrochloric acid (50 ml) and extracted with dichloromethane. The extract was evaporated to give a dark oil containing the title compound and its 3(E),5(E) isomer in the ratio 40:60. The isomers were separated by preparative reverse phase HPLC (on a $LP_1$-ODS silica column eluting with 85:15:0.1 methanol:wather:acetic acid) to give the title compound as a crystalline solid, m.p. 153°–155° C. MS (FAB) M+473.

EXAMPLE 38

Rel (1R,2S)-{3-[2-(2-Carboxyethylthio)-1-hydroxypentadeca3(E),5(E)-dienyl]phenyl}-1H-tetrazole The above compound was separated from the reaction described in Example 37(g).

EXAMPLE 39

(a) (1R,2R)-3-[2-(3-Methoxycarbonylphenylthio)-1-hydroxypentadeca-3(E),5(Z)-dienyl]-dienyl]-benzoic acid, methyl ester To a solution of methyl-3-mercaptobenzoate (0.42 g) in methanol (2 ml) under nitrogen was added triethylamine (0.38 ml) (development of light yellow colouration). The mixture was then transferred to another flask containing (1S,2S)-3-[1,2-oxido-pentadeca-3(E),5(Z)-dienyl]benzoic acid, methyl ester (0.8 g) under nitrogen. The reaction mixture was stirred at room temperature under nitrogen for 2 hours.

The volatiles were removed under a nitrogen stream and the residual oil purified by column chromatography (silica; eluant hexane 50% diethyl ether), to give the product as a light-yellow oil. (Proton NMR indicates predominantly (E),(Z) stereochemistry).

(b) (1S,2R)-3-[2-(3-Carboxyphenylthio)-1-hydroxypentadeca3(E),5(Z)-dienyl]benzoic acid To a solution of the diester (from step (a) (0.46 g) in tetrahydrofuran (2 ml) was added 2M lithium hydroxide solution (2.6 ml). The biphasic system was stirred vigorously for 20 hours at room temperature.

The tetrahydrofuran was removed in vacuo, and the aqueous phase cautiously acidified to pH4 with 2M hydrochloric acid. Extraction with chloroform, followed by drying (magnesium sulphate) and evaporation gave the title compound as a light-yellow solid, m.p. 90° (with resinification)

EXAMPLES 40–42

Similarly prepared, by the methods of Example 39 were the following:

(1S,2R)-3-[2-(4-Carboxyphenylthio)-1-hydroxypentadeca-3(E),5(Z) dienyl]benxoic acid (sticky yellow solid).

(1S,2R)-3-[2-(2-Carboxyphenylthio)-1-hydroxypentadeca-3(E),5(Z)-dienyl]benzoic acid (sticky solid).

(1S,2R)-3-[2-(butylthio)-1-hydroxypentadeca-3(E),5(Z)-dienyl]benzoic acid.

EXAMPLE 43

(a) (1S,2R)-3-[1-(3-Cyanophenyl)-1-hydroxypentadeca-3(E),5(Z)-dien-2-ylthio]benzoic acid, methyl ester To a solution of methyl-3-mercaptobenzoate (0.29 g) in methanol (1 ml) under nitrogen was added triethylamine (0.26 ml) (development of yellow colouration).

The mixture was then added to (1S,2S)-3-(1-oxidopentadeca-3(E),5(Z)-dienyl)benzonitrile (0.5 g) under nitrogen, and the reaction mixture stirred at room temperature for 4 hours.

The volatiles were removed under a nitrogen stream and the residual oil purified by chromatography (silica; eluant hexane/ether) to yield the product as a yellow oil.

(b) (1S,2R)-3-[1-(3-Cyanophenyl)-1-hydroxypentadeca-3(E),5(Z)dien-2-ylthio]benzoic acid To a solution of the methyl ester from step (a) (50 mg) in tetrahydrofuran (0.3 ml) was added 2M lithium hydroxide solution (0.15 ml), and the mixture stirred at room temperature for 24 hours.

The tetrahydrofuran was evaporated in vacuo, the aqueous phase acidified with 2M hydrochloric acid, and extracted twice with dichloromethane. Drying (magnesium sulphate) and evaporation of the organic extracts gave the title compound as a light-amber oil. (Proton NMR and reverse phase HPLC indicate about 30% of the (E),(E) isomer present.)

EXAMPLE 44

(a) 2,3-Oxido-3-phenylpropionaldehyde

To 50% hydrogen peroxide solution (16 ml), buffered with saturated sodium hydrogen carbonate solution) was added dropwise, with ice-bath cooling, a solution of cinnamaldehyde (26.4 g) in methanol (100 ml). The mixture was stirred at room temperature for 4 hours.

The methanol was removed in vacuo, and the aqueous phase extracted twice with toluene. The dried extracts were used, without isolation of the title compound, directly in step (b).

(b) 4,5-Oxido-5-phenyl-2-pentenal

The solution of 2,3-oxido-3-phenylpropionaldehyde in dry toluene (300 ml) from step (a) was treated with formylmethylene triphenyl phosphorane (60.8 g) and the mixture stirred at room temperature for 20 hours.

The reaction mixture was filtered and evaporated in vacuo, and the residual solid extracted three times with ether using an ultrasonic bath. The ether extracts were filtered and evaporated to give an oil which was further purified by column chromatography (silica; eluant hexane:ether, 1:1) to give the product as a yellow oil.

(c) 1,2-Oxido-1-phenylpentadeca-3(E),5(Z) -diene

To a solution of n-decyl-triphenylphosphonium bromide (20.54 g) in dry tetrahydrofuran (200 ml), cooled to −70° C. (dry ice/acetone bath) under nitrogen was added n-butyl lithium (26.6 ml of 1.6M hexane solution). There was immediate generation of orange colour of ylid. The mixture was stirred for 10 minutes, then a solution of 4,5-oxido-5-phenyl-2-pentenal (from step (b) in dry tetrahydrofuran (100 ml) added. The reaction mixture was allowed to warm to room temperature and stirred for 2 hours.

The tetrahydrofuran was evaporated in vacuo, the residual semi-solid extracted four times with diethyl ether using ultrasonification, and the extracts filtered and evaporated to give a yellow oil. This oil was further purified by chromatography (silica; eluant hexane:water, 1:1) to give the product as a mobile yellow oil, which crystallised upon cooling to −20° C. (m.p. <50° C.).

(d) Rel (1R,2S)-2-(2-Methoxycarbonylethylthio)-1-hydroxy-1-phenylpentadeca-3(E),5(Z)-diene To a solution of methyl-3-mercaptopropionate (0.44 g) in methanol (2 ml) under nitrogen was added triethylamine (0.5 ml). The mixture was transferred to a flask containing the epoxide from step (c) (1.00 g) under nitrogen. The reaction mixture was stirred for 20 hours, then further thiol (0.44 g) and triethylamine (0.5 ml) added.

After an additional 20 hours at room temperature the volatiles were removed under a nitrogen stream and the residue subjected to column chromatography (silica; eluant hexane:diethyl ether, 3:1), to give the title compound as a colourless oil.

(e) Rel (1R,2S)-2-(2-Carboxyethylthio)-1-hydroxy-1-phenylpentadeca-3(E),5(Z)-diene A mixture of the methyl ester from step (d) (0.49 g) tetrahydrofuran (3 ml) and 1M lithium hydroxide solution (3.5 ml) was stirred at room temperature for 24 hours.

The tetrahydrofuran was evaporated in vacuo, the aqueous phase acidified with 2M hydrochloric acid, and extracted twice with diethyl ether. The combined organic extracts were dried (magnesium sulphate) and evaporated to give the title compound as an amber oil.

EXAMPLE 45 (Alternative method)

(a) 3-[3-(2-Triphenylmethyl-2H-tetrazol-5-yl)phenyl]-2-propenol

To a solution of 3-[3-(1H-tetrazol-5-yl)phenyl]-2-propenol (2.02 g) in dry dichloromethane (50 ml) was added triethylamine (1.5 ml) followed by triphenylchloromethane (2.8 g) in dry dichlormethane. The solution was stirred at room temperature for 90 minutes, washed with water (50 ml), followed by sodium bicarbonate solution (5%; 50 ml), dried over magnesium sulphate, filtered and evaporated under reduced pressure to give a pale brown viscous oil which crystallised on standing to a cream solid.

(2S,3S)-3-[3-(2-Triphenylmethyl-2H-tetrazol-5-yl)phenyl]2,3-oxidopropanol

L-(+)-Dimethyl tartrate (1.85 g) was added in dry dichloromethane (10 ml) dropwise to a stirred solution of titanium (IV) isopropoxide (3.1 ml) in dry dichloromethane (30 ml) at −20° to −25° C. under nitrogen. The solution was stirred for 10 minutes and a solution of 3-[3-(2-triphenylmethyl-2H-tetrazol-5-yl)phenyl]-2-propenol (4.5 g) in dry dichlormethane (20 ml) was added, followed by a 3.7M solution of t-butylhydroperoxide in toluene (6.7 ml), both at −20° to −25° C. The pale orange solution was left to stand in a freezer for 3 hours. To the stirred solution was added aqueous tartaric acid (10%; 50 ml) and the mixture stirred for 1 hours, filtered and separated. The dichloromethane layer was dried over magnesium sulphate filtered and evaporated under reduced pressure to give a yellow oil. The oil was dissolved in carbon tetrachloride, washed with water, dried over magnesium sulphate, filtered and evaporated under reduced pressure to give a pale yellow oil. The oil was chromatographed on a silica gel column using diethyl ether and hexane (2:1) and the required fractions evaporated under reduced pressure to give a colourless crystalline solid.

(c) (4S,5S)-5-[3-(2-Triphenylmethyl-2H-tetrazol-5-yl)phenyl]-4,5-oxido-2-pentenal Solid-chromium trioxide (5.0 g) was added to a stirred solution of pyridine (7.9 ml) in dry dichloromethane (200 ml) at 5° C. The mixture was stirred for 45 minutes, warming to 13° C., allowing all the chromium trioxide to dissolve, then a solution of the epoxyalcohol of step (b) (4.61 g) in dry dichloromethane (50 ml) was added rapidly. The dark mixture was stirred for 90 minutes, warming to room temperature, then filtered through a pad of Florisil to remove the chromium salts, and the colourless filtrate was evaporated under reduced pressure to leave a pale yellow oil.

To a solution of the oil (1.8 g) in benzene (75 ml) under nitrogen, was added formylmethylenetriphenylphosphorane (1.34 g) in one portion. The suspension was stirred at room temperature under nitrogen for eight hours, unreacted ylid was filtered off and the filtrate evaporated under reduced pressure to a brown oil. The brown oil was extracted with hot ether, cooled, filtered and evaporated under reduced pressure to give a yellow oil, which crystallised on standing to give a yellow solid.

(d) (1S,2S)-5-{3-[2-(1,2-Oxido)pentadeca-3(E),5(Z)-dienyl ]phenyl}-2-triphenylmethyl-2H-tetrazole n-Butyl lithium (8.91 ml; 1.5M) in hexane was added dropwise to a stirred solution of n-decyl triphenylphosphonium bromide (6.07 g) (dried at 80° C. under reduced pressure for 16 hours) in dry tetrahydrofuran (130 ml) at −70° C. under nitrogen. The clear deep orange solution obtained was stirred for a further 10 minutes at −70° C., then a solution of 5-[3-(2-triphenylmethyl-2H-tetrazol-5-yl)phenyl]-4,5-oxido-2-pentenal (6.4 g) in dry tetrahydrofuran (75 ml) was added dropwise. The pale yellow solution was stirred at −70° C. for 1 hour, allowed to warm at room temperature and evaporated under reduced pressure to a brown oil. The oil was extracted with ether:hexane (1:2; 4×200 ml) and the pale hazy extract evaporated under reduced pressure to give the title compound as a yellow oil.

(e) (1S,2R)-5-{3-[2-(2-Methoxycarbonylethylthio)-1-hydroxypentadeca-3(E),5(Z)-dienyl]phenyl}-2-triphenylmethyl-2H -tetrazole.

A solution of (1S,2S)-5-{3-[2-(1,2-oxido)pentadec-3(E),5(Z)-dienyl]phenyl}-2-triphenylmethyl-2H-tetrazole (4.5 g) and triethylamine (2.06 ml) in methanol (15 ml) was placed in a flask under nitrogen. This solution was then added to methyl 3-thiopropionate (900 mg) under nitrogen and the solution was then stirred for 24 hours at room temperature until reaction was complete. The solution was evaporated under reduced pressure to leave a brown oil which was chromatographed on a silica column using ether:hexane (1:1). The required fractions were evaporated under reduced pressure to give the title compound as a yellow oil.

(f) (1S,2R)-5-{3-[2-(2-Carboxyethylthio)-1-hydroxypentadeca-3(E),5(Z)-dienyl]phenyl}-1H-tetrazole, sodium salt (1S,2R)-5-{3-[2-Methoxycarbonylethylthio)-1-hydroxypentadeca-3(E),5(Z)-dienyl]phenyl}-2-triphenylmethyl-2H-tetrazole (2.74 g) was dissolved in ether (50 ml) to which was added aqueous hydrochloric acid (20 ml; 5M) and the mixture stirred at room temperature for 4 hours, when t.l.c. showed the loss of triphenylmethyl protection was completed. The ether was evaporated under reduced pressure, tetrahydrofuran (30 ml) was added, followed by the addition of aqueous lithium hydroxide (2M) until the solution was alkaline. The mixture was then left to stir overnight at room temperature. The aqueous basic phase was then separated, acidified with aqueous hydrochloric acid (2M), extracted with ether (2×50 ml) and the ether extract evaporated under reduced pressure to give a brown oil. The oil was chromatographed on a silica column using ether and the required fraction evaporated under reduced pressure to give a pale yellow oil. The oil was dissolved in aqueous sodium bicarbonate (0.5M; 1 eq) and freeze-dried to give the sodium salt.

In the formulating the active compounds of the invention, they are preferably employed in salt form. The following formulations are given by way of example:

EXAMPLE 46

Soft gelatin capsule
Each soft gelatin capsule contains:

| | |
|---|---|
| Active ingredient | 150 mg |
| Arachis oil | 150 mg |

After mixing together, the blend is filled into soft gelatin capsules using the appropriate equipment.

EXAMPLE 47

Hard gelatin capsule
Each capsule contains

| | |
|---|---|
| Active ingredient | 50 mg |
| PEG 4000 | 250 mg |

The PEG 4000 is melted and mixed with the active ingredient. Whilst still molten the mixture is filled into capsule shells and allowed to cool.

EXAMPLE 48

Aerosol

| | |
|---|---|
| Active ingredient | 10 mg |
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminum cans for inhalation aerosols. The cans are degassed with propellant 12 and sealed with an appropriate metered dose valve. The volume of product expelled per actuation is 50 to 100 μl equivalent to 0.5–1 mg active ingredient.

We claim:

1. A compound of the formula

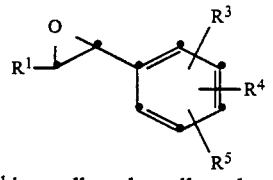

ps in which $R^1$ is an alkenyl or alkynyl group *containing from 10 to 20 carbon atoms and* optionally substituted with a phenyl group or phenyl group substituted with 1–3 substituents selected from the group consisting of $C_1$–$C_4$alkyl, $C_1$–$C_4$alkoxy, hydroxy, nitro, cyano, halo, trifluoromethyl, carboxyl, tetrazolyl, and —$CONH_2$, [and containing from 5 to 30 carbon atoms,] and $R^3$, $R^4$ and $R^5$ are each selected from hydrogen, carboxyl, $C_2$-$C_5$alkoxycarbonyl, $C_1C_4$alkyl, $C_1$–$C_4$alkoxy, hydroxyl, tetrazolyl, tetrazolyl protected with a trityl or benzhydryl group, halo, trifluoromethyl, nitrile, nitro and $CONR_2{}^{10}$ where each $R^{10}$ is hydrogen or $C_1$–$C_4$ alkyl; and salts thereof.

2. The compound of claim 1 which is (1S,2S)-5-{3-[2-(1,2-oxido)pentadeca-3(E),5(Z)-dienyl]phenyl}-2-triphenylmethyl-2H-tetrazole.

* * * * *